United States Patent [19]
Gelbfish

[11] Patent Number: 5,662,603
[45] Date of Patent: Sep. 2, 1997

[54] MEDICAL MATERIAL REMOVAL METHOD AND ASSOCIATED INSTRUMENTATION

[76] Inventor: Gary A. Gelbfish, 2502 Ave. I, Brooklyn, N.Y. 11210

[21] Appl. No.: 654,834

[22] Filed: May 29, 1996

[51] Int. Cl.$^6$ .................................................. A61B 17/32
[52] U.S. Cl. ............................ 604/22; 606/167; 606/170
[58] Field of Search ............................ 604/22, 35, 49, 604/19; 606/167–171, 178–180

[56] References Cited

U.S. PATENT DOCUMENTS

| | | |
|---|---|---|
| Re. 33,258 | 7/1990 | Onik et al. . |
| 2,708,437 | 5/1955 | Hutchins . |
| 3,173,414 | 3/1965 | Guillant . |
| 3,732,858 | 5/1973 | Banko . |
| 3,844,272 | 10/1974 | Banko . |
| 4,030,503 | 6/1977 | Clark, III . |
| 4,589,414 | 5/1986 | Yoshida et al. . |
| 4,620,547 | 11/1986 | Boebel . |
| 4,669,469 | 6/1987 | Gifford, III et al. . |
| 4,678,459 | 7/1987 | Onik et al. . |
| 4,747,821 | 5/1988 | Kensey et al. . |
| 4,819,635 | 4/1989 | Shapiro . |
| 4,846,192 | 7/1989 | MacDonald . |
| 4,900,300 | 2/1990 | Lee . |
| 4,913,698 | 4/1990 | Ito et al. . |
| 4,936,845 | 6/1990 | Stevens . |
| 4,986,807 | 1/1991 | Farr . |
| 4,994,067 | 2/1991 | Summers . |
| 5,052,999 | 10/1991 | Klein . |
| 5,106,364 | 4/1992 | Hayafuji et al. . |
| 5,122,153 | 6/1992 | Harrel . |
| 5,286,253 | 2/1994 | Fucci . |
| 5,368,603 | 11/1994 | Halliburton . |
| 5,368,635 | 11/1994 | Smith . |
| 5,395,313 | 3/1995 | Naves et al. . |
| 5,601,582 | 2/1997 | Shelton et al. ..................... 604/22 X |
| 5,601,583 | 2/1997 | Donahue et al. ...................... 606/170 |

FOREIGN PATENT DOCUMENTS 2 018 601  10/1979  United Kingdom .

OTHER PUBLICATIONS

Peyman, et al., Arch Ophthal., Experimental Vitrectomy, vol. 86, Nov. 1971.

*Primary Examiner*—John D. Yasko
*Attorney, Agent, or Firm*—McAulay Fisher Nissen Goldberg & Kiel, LLP

[57] ABSTRACT

A cutting member for a medical material removal instrument comprises a cutting head having an axis and an elongate drive rod eccentrically attached at a distal end to the cutting head at a location spaced from the axis. The drive rod extends substantially parallel to the axis. The cutting member is used with an introducer sheath or catheter which has a distal end portion inserted into a patient. The cutting head is provided with a cut-out on the proximal side in part for enabling a drawing of material in a proximal direction internally from a patient into a distal end of the sheath upon a partial ejection of the cutting head from the distal end of the sheath during a material removal operation. The material drawn into the sheath is severed in a scissors-type action of the cutting head against the distal end of the sheath upon a drawing of the cutting head via the drive rod into the distal end of the sheath. The cutting head has a maximal transverse cross-section conforming in a close fit to an inner surface of the sheath and is tapered from the maximal transverse cross-section in a proximal direction to facilitate a smooth and unobstructed drawing of the cutting head into the distal end of the sheath and also without damaging the sheath. The cutting head has an at least approximately semicylindrical outer surface located between the maximal transverse cross-section and a most proximal end of the cutting head. The semicylindrical outer surface serves to ensure a locating of the drive rod eccentrically relative to the sheath upon the drawing of the cutting head into the distal end of the sheath. Irrigation is optionally provided to aid in clot removal.

23 Claims, 2 Drawing Sheets

MEDICAL MATERIAL REMOVAL METHOD AND ASSOCIATED INSTRUMENTATION

BACKGROUND OF THE INVENTION

This invention relates to a method and an associated device for removing material internally from a patient. Even more specifically, this invention relates to a thrombectomy device for use with radiology introducer sheaths and catheters.

Clot (thrombus) in the vascular system is a frequently encountered clinical problem in medicine. Obstruction of the human vascular system by clot in both the arterial and venous systems is the cause of much morbidity and mortality.

The location of such clot or other vascular obstructions are usually diagnosed by the performance of an angiogram. During this procedure, dye is injected into the vascular system, permitting the visualization of the vascular tree by fluoroscopic imaging.

In almost all cases of radiological vascular diagnosis or treatment, a device called an "introducer sheath" is used. These sheaths are inserted using a multistage "Seldinger technique" at the beginning of the procedure and they remain in place for the duration of the procedure. They permit guide wires, catheters and various instruments to be repetitively and easily inserted and withdrawn without losing access to the vascular system. Once the sheath is removed it cannot be reinserted without repeating the entire Seldinger technique.

Introducer sheaths frequently incorporate other components to enhance their function. A self sealing "hemostasis valve" permits the insertion of devices into the sheath, and seals around the respective catheters so that bleeding does not occur around them. This valve also closes completely once the catheter has been removed so that bleeding through the sheath is avoided. A "side port" in direct communication with the sheath lumen permits the infusion of saline or other fluids into the body during the performance of the procedure and also permits suction to be transmitted to the sheath lumen.

When clot is identified in the vascular system, one of several approaches may be used depending on clinical indications.

The use of catheters to aspirate clot via suction is perhaps the most intuitive approach. Handley in 1907 was the first to describe such an attempt with clot at the bifurcation of the aorta. In his case report, a suction catheter was threaded upwards through a groin incision, but failed to remove significant amounts of clot. It was subsequently necessary to employ mechanical maceration and forcible saline irrigation in conjunction with the native aortic pressure to expel the clot and restore flow.

The use of suction, applied to a catheter or radiological introducer sheath side port in an attempt to remove clot, is a known clinical maneuver. It is only applicable, however, to partially lysed and "soupy" clot and its success is directly related to the cross sectional internal lumen the sheath or catheter. Even if large-bore catheters (8–12 Fr.) are used, which are undesirable for use in the vascular system, this maneuver is usually only partially successful since clot forms an obstruction at the tip of the sheath or catheter. Despite their size, these catheters need repetitive removal from the body for cleansing secondary to clogging, an option not available for the introducer sheath which must remain in place for the entire procedure.

It should be noted that introducer sheaths and catheters may both be used for the purpose of aspirating clots or other viscous material. Each have their own benefits and disadvantages. Catheters may be withdrawn and cleaned, an option not available with sheaths, while introducer sheaths provide for the largest cross sectional lumen, without being decreased by a catheter inserted through them. The device described herein in accordance with the invention may be used with both, however, it is envisioned for primary use with introducer type sheaths which have the hemostatic valve and side port necessary for optimal use of the device described herein. Of course, the device of the present invention may be complete in itself, with a dedicated outer tube performing functions of the above-discussed introducer sheath.

A March 1996 report by Sharafuddin et al. in the Journal of Vascular and Interventional Radiology describes a method of clot removal through introducer sheaths. A balloon catheter (Fogarty) is used to aid in this process. The balloon catheter is inserted through the sheath and is inflated behind the clot. The balloon is then withdrawn pressurizing and forcing the clot into the sheath, while suction is simultaneously applied to the sheath. This report is significant as it illustrates the heretofore unsolved problems with these techniques that severely limit their applicability. This includes the potentially dangerous maneuver of pressurizing the clot in the vascular vessel in order to effect its removal. Also the procedure is likely to be extremely inefficient because a centrally located and obstructing Fogarty catheter shaft is always located in the path of clot removal.

Previous techniques to remove clot through sheaths, including corkscrew type devices, rods with balls at the tip. etc. have been described. These too are limited by the inevitable obstruction of the tureen by the device rod which will wobble especially at the tip of the sheath. This constant obstruction, at times centrally placed within the introducer sheath, severely limits the efficiency of clot removal through the reduction of the effective cross sectional diameter available for the collection and transportation of clot. Furthermore, it interferes with the ability of the applied suction to catch and draw in a segment of clot since it is difficult to form a seal around this shaft; a necessary condition when entrapping and suctioning clot. Without this seal, blood loss may be increased since blood will be aspirated preferentially instead of the clot.

Because of these inherent and previously insurmountable problems, suction thrombectomy is not a commonly practiced technique in clinical medicine. The challenge remains how to remove clot through relatively small bore tubes (5–7 Fr.) without clogging and without repetitive removal for cleaning.

Besides suction thrombectomy, multiple mechanical methods for clot removal have been proposed. These devices rely on one of several mechanisms to disrupt and macerate clot including rotating baskets, wires, water jets and cutters of various configurations. These devices are all limited by complexity, cost and clot fragment embolization and have not yet found widespread use in clinical medicine.

Because of these limitations, open surgery, clot-lysis via urokinase and long-term treatment with blood thinners remain the primary methods of treatment today for clot in the vascular system. All these modalities have short- and long-term disadvantages.

Certainly a method and device that would enable the extraction of clot through introducer sheaths or simple suction catheters would significantly enhance the treatment options for these patients.

OBJECTS OF THE INVENTION

A general object of the present invention is to provide an improved method and an associated device for removing material such as clot from a patient.

It is a more particular object of this invention to provide a device for extraction of material (e.g., clot) from a patient through a standard radiology introducer sheath, such that the larger lumen of these sheaths can be used.

Another object of the present invention is to provide a device that, when placed within the lumen of an introducer sheath, decreases, by the smallest amount possible, the available transverse cross-sectional diameter so that clot removal efficiency can be maximized.

An additional object of the present invention is to provide a such device with a configuration that will permit suction to form an effective seal between the clot and device such that clot removal efficiency is maximized and blood loss is minimized.

Yet another object of the present invention is to provide a device of minimal complexity, number of components and energy requirements so that cost, the potential for device failure and potential for patient harm may also be minimized.

A further object of the present invention is to provide a device that may be left in place in the introducer sheath, yet still permit the simultaneous introduction of other catheter and guide wires for diagnostic and treatment maneuvers.

These and other objects of the present invention will be apparent from the drawings and detailed descriptions herein.

BRIEF DESCRIPTION

In accordance with an embodiment of the present invention, a cutting member for a medical material removal instrument comprises a cutting head having an axis and an elongate drive rod eccentrically attached at a distal end to the cutting head at a location spaced from the axis. The drive rod extends substantially parallel to the axis. The cutting member is used with an introducer sheath or catheter which has a distal end portion inserted into a patient. The cutting head is provided with a cut-out on the proximal side in part for enabling a drawing of material in a proximal direction internally from a patient into a distal end of the sheath upon a partial ejection of the cutting head from the distal end of the sheath during a material removal operation. The material drawn into the sheath is severed in a scissors-type action of the cutting head against the distal end of the sheath upon a drawing of the cutting head via the drive rod into the distal end of the sheath. The cutting head has a maximal transverse cross-section conforming in a close fit to an inner surface of the sheath and is tapered from the maximal transverse cross-section in a proximal direction to facilitate a smooth and unobstructed drawing of the cutting head into the distal end of the sheath and also without damaging the sheath. The cutting head has an at least approximately semicylindrical outer surface located between the maximal transverse cross-section and a most proximal end of the cutting head. The semicylindrical outer surface serves to ensure a locating of the drive rod eccentrically relative to the sheath upon the drawing of the cutting head into the distal end of the sheath.

Where the drive rod has a longitudinally extending lumen, an irrigation outlet is provided in one of the cutting head and the drive rod at a distal end thereof. In general, the irrigation outlet is provided at a most distal position so that irrigation fluid is always delivered to the sheath at a point upstream of any severed material in the sheath. The cutting head closes the distal end of the sheath upon the termination of a proximally directed cutting stroke. The feeding of fluid upstream of the severed material and a continued application of suction downstream of the severed material enables the formation of a pressure differential across the severed mass, thereby greatly facilitating the removal of the severed mass from the introducer sheath and from the patient. Conceptually, each time a reciprocation is made and the device is cleared, it is functionally equivalent to the laborious removal of a traditional suction catheter from the body, cleansing it, reinserting and repositioning it within the body.

According to a specific embodiment of the present invention, the cutting member further comprises an annular balloon attached to the cutting head on a distal side thereof. A channel is provided for delivered fluid to the balloon for inflating the balloon. The balloon pressurization fluid may be delivered through a separate duct or, alternatively, through the irrigation lumen in the drive rod. In the latter case, a valve is advantageously provided at the distal end of the drive rod and/or in the cutting head for blocking the irrigation outlet (to the sheath) and opening a fluid flow pathway to the balloon. The valve may be spring loaded and opened by exerting tension on a wire which traverses the lumen of the drive rod.

Where the cutting head is hollow, the irrigation outlet is preferably located in the cutting head.

The cutting head is preferably provided with a rounded distal end and in that event has a bullet shape.

A medical method for removing material internal to a patient comprises, in accordance with the present invention, (I) inserting a distal end portion of an introducer sheath into a patient, while maintaining a proximal end portion of the sheath outside the patient, and (II) inserting a cutting head with a drive rod eccentrically attached to a proximal side thereof into the sheath. The drive rod is automatically disposed eccentrically inside the sheath in part by virtue of the eccentric attachment of the drive rod to the cutting head. After insertion of the distal end portion of the sheath into the patient, at least a distal end portion of the cutting head is ejected from the sheath through an aperture in a distal end face of the sheath, thereby opening the aperture. Suction is applied to the sheath to pull material from the patient into the sheath through the opened aperture. Thereafter the drive rod is pulled in a proximal direction to retract the cutting head into the sheath through the aperture, thereby severing material in the sheath from material outside the sheath. The drive rod again is automatically disposed eccentrically inside the sheath in part by virtue of the eccentric attachment of the drive rod to the cutting head. Suction is applied to the sheath to remove the severed material from the sheath.

In accordance with another feature of the present invention, the method includes inserting a distal end portion of an ancillary instrument into the patient through the sheath and the aperture after the cutting head has been at least partially ejected from the sheath through the aperture. The ancillary instrument is actuated from outside the patient to effectuate an operation on material inside the patient. Subsequently, the ancillary instrument is pulled in a proximal direction through the sheath to remove the ancillary instrument from the patient.

Where the ancillary instrument includes a collapsed balloon at a distal end, the method further comprises inflating the balloon inside the patient. The actuating of the ancillary instrument then includes pulling the inflated balloon in a proximal direction towards the sheath, thereby drawing material internal to the patient towards the aperture.

As discussed above, irrigation fluid is advantageously fed to the sheath via the drive rod to a location in the sheath distally of the severed material to cooperate with the applied suction to form a pressure gradient across the severed material, thereby facilitating removal of the severed material from the sheath.

A cutting member in accordance with the present invention is designed to facilitate the guidance of an ejected cutting head back into the distal end of the catheter or guide tube without jamming or catching and to automatically locate the drive rod eccentrically with respect to the catheter or guide tube so that the cross-sectional areas of the catheter or guide tube available for clot removal is maximized. This automatic guidance of the ejected cutting head and the automatic "eccentering" of the drive rod are accomplished simply by the design of the cutting member. The guide tube or introducer sheath need have no septa or other guide elements. The guide tube or sheath is unencumbered and simplified, even when included as an integral part of a dedicated thrombectomy assembly.

A device in accordance with the preset invention enables extraction of material such as thrombus from a patient through a standard radiology introducer sheath. The cross-sectional area of the material removal path is maximized inasmuch as the number of walls, septa and channels is minimized and permits use of simple, readily available tubes. The device has a configuration which permits sucked-in clot material to fill the suction path, thereby forming an effective seal with the walls of that path so that clot efficiency is maximized and blood loss is minimized.

A device in accordance with the invention is of simple construction, with a minimal number of components and small energy requirements. Consequently, the cost, the potential for device failure and potential for patient injury are all reduced. The device that may also be left in place in the introducer sheath, yet still permit the simultaneous introduction of other catheters and guide wires for diagnostic and treatment maneuvers, thus minimizing the number of steps and time necessary to complete interventional procedures.

Accordingly, a device in accordance with the present invention is designed to maximize the efficiency of clot removal through the smallest diameter tubes. It is further designed to minimize device complexity and cost, to minimize clot maceration and embolization and to obviate the need of drive motors or other high energy sources under most clinical circumstances.

DESCRIPTION OF THE PREFERRED EMBODIMENTS

Figure 1:
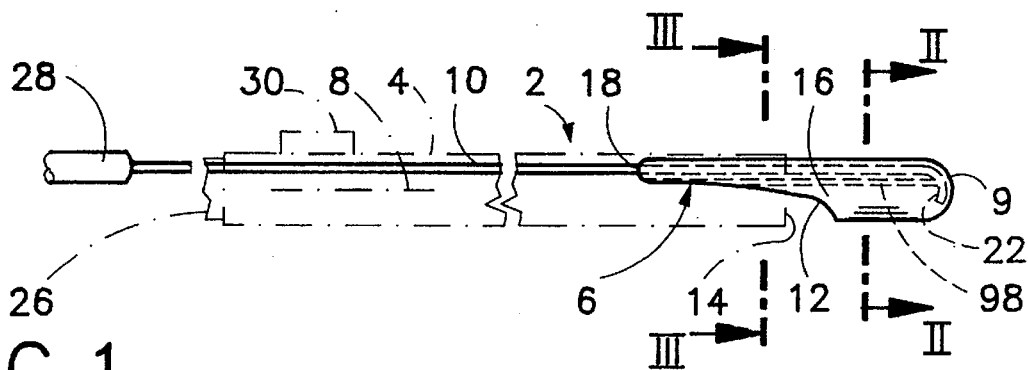
FIG. 1 is a schematic side elevational view, on an enlarged scale, of a thrombectomy device for use with an introducer sheath, in accordance with the present invention.
Figures 2, 3:
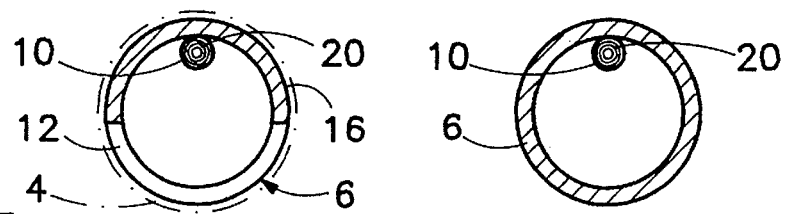
FIG. 2 is a cross-sectional view taken along line II—II in FIG. 1.
FIG. 3 is a cross-sectional view taken along line III—III in FIG. 1.

As illustrated in FIGS. 1–3, a thrombectomy device 2 utilizable with a standard vascular introducer sheath 4 for removing clot material from a vascular component or graft comprises a cylindrical cutting head 6 having a longitudinal axis 8 and a rounded distal end 9. An elongate drive rod 10 is eccentrically attached at a distal end to cutting head 6 at a location spaced from axis 8. Drive rod 10 extends parallel to axis 8. Cutting head 6 is provided on a proximal side with a cutout 12 in part for enabling a drawing of thrombus in a proximal direction internally from a patient into a distal end of sheath 4 upon a partial ejection of cutting head 6 through an aperture 14 in the distal end of sheath 4 during a thrombectomy procedure. The material drawn into sheath 4 is severed by cutting head 6 in a scissors-like action upon a drawing of cutting head 6 via drive rod 10 into the distal end of sheath 4.

Cutting head 6 has a semicylindrical outer surface 16 which closely conforms to an inner surface of sheath 4. Surface 16 may begin at a point which is longitudinally spaced from the most proximal end point 18 of cutting head 6 and is located between a maximal transverse cross-section of cutting head 6 (at line II—II in FIG. 1) and proximal end point 18. In FIG. 1 and 3, surface 16 is located in a region about the distal end face or distal aperture 14 of sheath 4. Surface 16 extends generally from drive rod 10 on one side of cutting head 6 to cutout 12 on an opposite side of cutting head 6 and serves to ensure a locating of drive rod 10 eccentrically relative to sheath 4 upon the drawing of cutting head 6 into the distal end of sheath 4. This locating is effectuated by the close fit of the cutting head into the introducer sheath and the inability of the cutting head to migrate in a transverse or radial direction relative to the sheath once semicylindrical surface 16 of cutting head 6 has been drawn into the sheath. Also, the construction of the proximal end portion of cutting head 6, as tapered from the maximal cross-section (line II—II) to proximal end point 18, enables an unobstructed and smooth guiding of the cutting head 6 into sheath 4 through aperture 14, without catching.

Drive rod 10 has a longitudinally extending lumen 20 (FIGS. 2 and 3) and extends into cutting head 6 along an inner surface (not designated) thereof to a distal end of the cutting head. At that distal end, drive rod 10 is provided with an irrigation outlet 22 which communicated with lumen 20. In general, irrigation outlet 22 is provided at a most distal position of device 2 so that irrigation fluid is always delivered to sheath 4 at a point upstream of any severed mass 24 (FIG. 4) in sheath 4.

During a thrombectomy procedure, a distal end portion of sheath 4 is inserted into a vascular component or vascular graft. Cutting head 6, together with a distal end portion of tubular drive rod 10, is then inserted through a port 26 at a proximal end of the introducer sheath. Drive rod 10 is provided at a proximal end with a handle 28 for facilitating the manipulation of the device 2 during the thrombectomy procedure.

Figure 4:
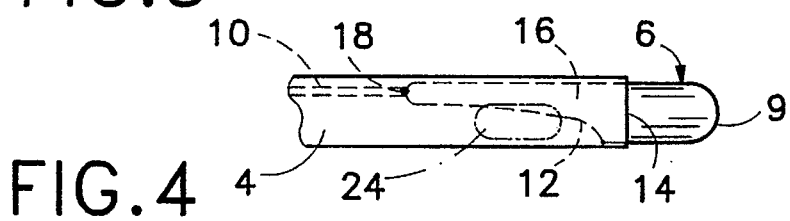
FIG. 4 is a schematic side elevational view, on an enlarged scale, of the thrombectomy device of FIG. 1, showing the device withdrawn into a distal end of an introducer sheath.

Cutting head 6 is ejected from aperture 14, as depicted in FIG. 1. Suction applied to sheath 4 via a suction port 30 pulls thrombus from the patient into sheath 4 via aperture 14 and a window defined by cutout 12. Subsequently, cutting head 6 is retracted into sheath 4, as illustrated in FIG. 4, thereby severing clot mass 24. Cutting head 6 also closes the distal end of sheath 4 upon the termination of the proximally directed cutting stroke. Suction is applied continuously via port 30, while irrigation fluid is fed to cutting head 6 and consequently to sheath 4 via lumen 20 and irrigation outlet or port 22. The feeding of fluid upstream of severed clot mass 24 and a continued application of suction downstream of the severed material enables the formation of a pressure differential across the severed mass, thereby greatly facilitating the removal of the severed mass from introducer sheath 4 and from the patient. An alternative procedure is to mechanically pull clot out of introducer sheath 4 via drive rod 10 and cutting head 6. Consequently, drive rod 10 may be a solid, but flexible, member with irrigation outlet or port 22 omitted.

Figure 5:
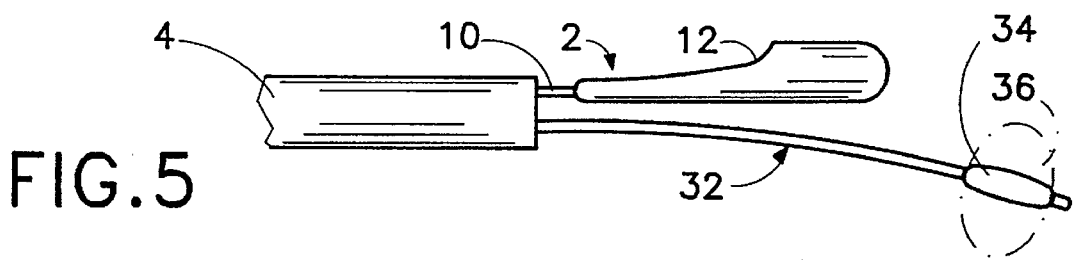
FIG. 5 is a schematic side elevational view, on an enlarged scale, of the thrombectomy device of FIG. 1, showing a distal end of the device ejected from the introducer sheath of FIGS. 1 and 4 and an ancillary balloon instrument deployed.

As illustrated in FIG. 5, cutting head 6 may be ejected entirely from sheath 4 and turned about axis 8, thereby enabling the insertion of a distal end portion of an ancillary instrument 32 into the patient through sheath 4 and aperture 14. Ancillary instrument 32 is then actuated from outside the patient to effectuate an operation on material such as thrombus or tissue inside the patient. Subsequently, instrument 32 is pulled in a proximal direction through sheath 4 to remove the instrument from the patient. In FIG. 5, ancillary instrument 32 specifically takes the form of a Fogarty catheter with a balloon 34 which may be inflated into an expanded configuration 36 and pulled in a proximal direction towards sheath 4, thereby drawing thrombus internal to the patient towards aperture 14.

Figure 6:
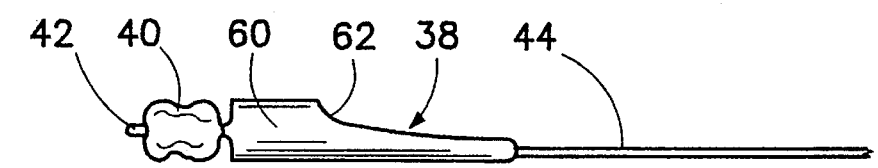
FIG. 6 is a schematic side elevational view, on an enlarged scale, of another thrombectomy device for use with an introducer sheath, in accordance with the present invention, showing a balloon in a collapsed configuration at the distal end of the device.

As depicted in FIG. 6, a hollowed cutting head 38 on a thrombectomy device similar to device 2 includes an annular balloon 40 attached to cutting head 38 on a finger extension 42 provided on a distal side of cutting head 38. The thrombectomy device of FIG. 6 may itself be used to move clot through a vascular component or graft.

Figure 7:
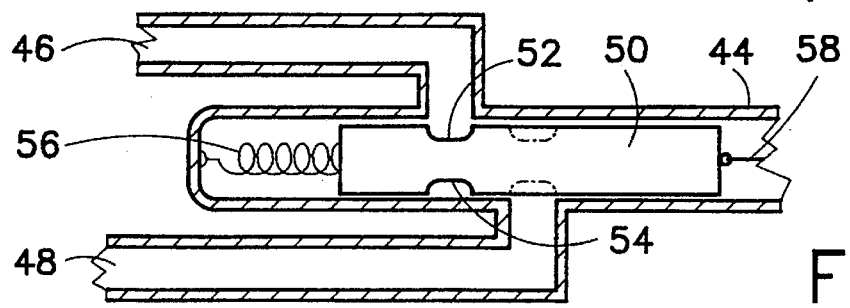
FIG. 7 is a schematic cross-sectional view, on an enlarged scale, showing a spring loaded valve provided in the device of FIG. 6 for alternatively feeding irrigation fluid to an introducer sheath or to the balloon of FIG. 6.

As shown in FIG. 7, a hollow or tubular drive rod 44 (see also FIG. 6) which is mechanically fastened to cutting head 38 is provided at a distal end with a pair of branches 46 and 48. One branch 46 extends inside an inner surface of cutting head 38 to a distal end of that inner surface and is provided with an irrigation outlet (not shown) for supplying irrigation fluid to an introducer sheath (e.g., 4) after a cutting phase of an operating cycle during a thrombectomy procedure. The other branch 48 communicates with balloon 40 (FIG. 6) for providing irrigation fluid thereto to pressurize and inflate the balloon. A sleeve valve 50 is slidably disposed inside drive rod 44 at a distal end thereof for regulating the flow of fluid to branches 46 and 48. More particularly, sleeve valve 50 is provided with a first aperture 52 alignable with branch 46 at an inlet end thereof during a thrombus cutting operation to channel irrigation fluid to the surrounding introducer sheath for assisting in the removal of a severed thrombus mass. Sleeve valve 50 is further provided with a second aperture 54 alignable with branch 48 at an inlet end thereof to enable the pressurization and expansion of balloon 40. A spring 56 biases sleeve valve 50 in the distal direction to align aperture 52 with branch 46. To inflate (or deflate) balloon 40, a wire 58 attached to sleeve valve 40 is pulled to shift the sleeve valve in a proximal direction. Wire 58 longitudinally traverses drive rod 44.

It is to be noted that drive rods 10 and 44 are automatically disposed eccentrically inside sheath 4 in part by virtue of the eccentric attachment of drive rods 10 and 44 to cutting heads 6 and 38, respectively. Cutting heads 6 and 38 preferably have at least approximately semicylindrical outer surface 16 and 60 extending from drive rods 10 and 44 on one side of cutting heads 6 and 38 to cutouts 12 and 62 on an opposite side of the respective cutting head. Outer surfaces 16 and 60 of cutting heads 6 and 38 are The at least approximately semicylindrical and conform substantially to an inner surface of sheath 4 to ensure a locating of drive rods 10 and 44 eccentrically relative to sheath 4 upon a drawing of cutting heads 6 and 38 into sheath 4, thereby maximizing a cross-sectional area of sheath 4 during suction operation.

Figure 8:
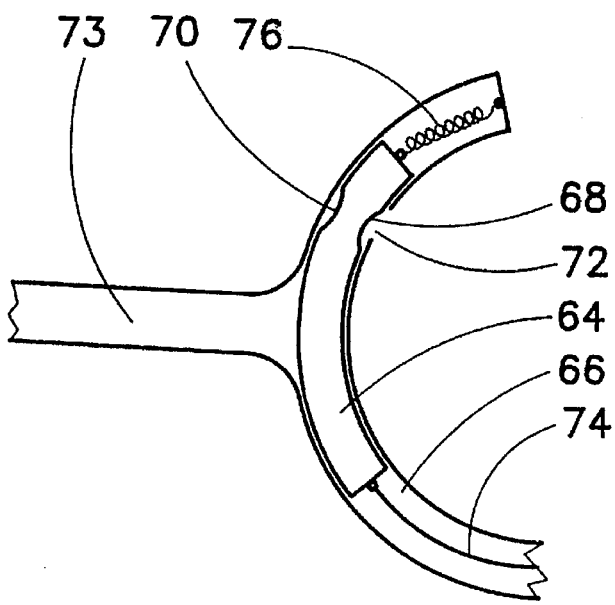
FIG. 8 is a schematic cross-sectional view, on an enlarged scale, showing another spring loaded valve for alternatively feeding irrigation fluid to an introducer sheath or to the balloon of FIG. 6.

FIG. 8 shows an arcuate sleeve valve 64 slidably disposed inside an arcuate channel 66 communicating with a drive rod (not shown) of a thrombectomy cutting head. Sleeve valve 64 has a pair of apertures 68 and 70 alternately alignable with an irrigation outlet 72 and a balloon infeed duct 73. Sleeve valve 64 is shifted by a wire 74 in opposition to a returning force provided by a biasing spring 76.

Figure 9:
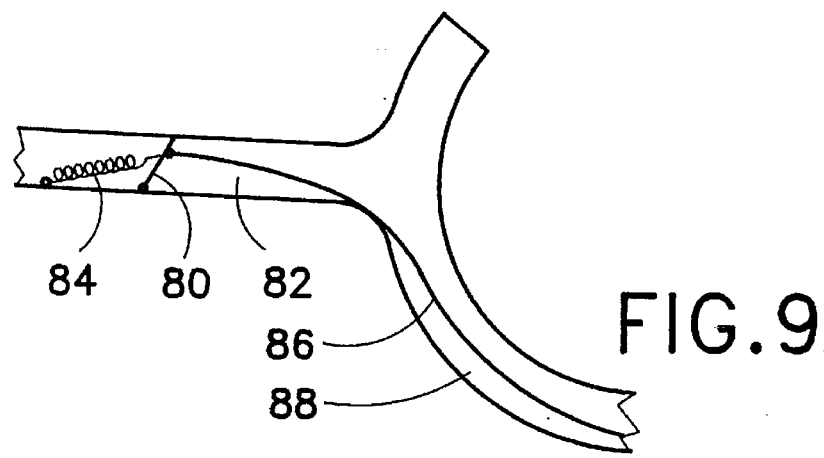
FIG. 9 is a schematic cross-sectional view, on an enlarged scale, showing yet another spring loaded valve for alternatively feeding irrigation fluid to an introducer sheath or to the balloon of FIG. 6.

FIG. 9 shows a valve member 80 disposed in a balloon infeed duct 82 and biased in a closed position by a tension spring 84. A valve actuating wire 86 extends from valve member 80 back through a lumen 88 of a drive rod.

Figure 10:
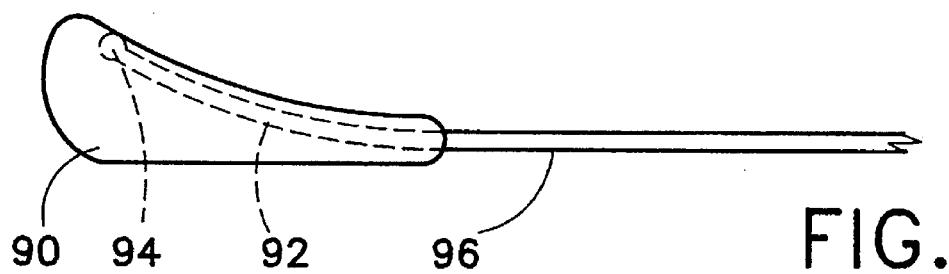
FIG. 10 is a schematic partial side elevational view, on an enlarged scale, showing et a further thrombectomy device utilizable with a standard introducer sheath, in accordance with the present invention.

FIG. 10 depicts a cutting head 90 similar to cutting head 6, except that cutting head 90 is solid instead of hollow. A channel 92 extends through cutting head 90 to an irrigation outlet 94 for guiding irrigation fluid from a drive rod 96 to irrigation outlet 94.

Cutting heads 6 and 38, as well as other thrombectomy members disclosed hereinabove, may be positioned with conventional guide wires in accordance with well known techniques. The guide wires may be inserted through an additional lumen (other than lumen 20, FIGS. 2 and 3), or through a separate channel 98 (FIG. 1) provided in cutting head 6 or 38. Alternatively, a guide wire may be integrally attached to cutting head 6 or 38, for instance, by a weld.

Although the invention has been described in terms of particular embodiments and applications, one of ordinary skill in the art, in light of this teaching, can generate additional embodiments and modifications without departing from the spirit of or exceeding the scope of the claimed invention. For example, where a balloon 40 is attached to the distal end of a cutting head 38, the balloon may be inflated and deflated via a separate duct, different from the irrigation channel in the drive rod. Also, many equivalent valve designs are available to one skilled in the art for permitting the use of the irrigation channel in the cutting member drive rod for the pressurization of the balloon on the cutting head. One alternative design is to provide a spring loaded valve which may be opened by pushing on a guide wire disposed in the lumen of the drive rod.

A device in accordance with the invention may be used in internal organs other than blood vessels or vascular prostheses to remove material other than blood clots. However, the device is particularly effective in performing thrombectomies and removing other semi-solid and viscous materials such as adipose tissue or intraocular material.

It is to be observed that an implanted prosthetic device such as a vascular bypass made of synthetic materials is considered to be a vascular organ for purposes of the invention.

Accordingly, it is to be understood that the drawings and descriptions herein are proffered by way of example to facilitate comprehension of the invention and should not be construed to limit the scope thereof.

What is claimed is:

1. A cutting member for a medical material removal instrument, comprising a cutting head having an axis and an elongate drive rod eccentrically attached at a distal end to said cutting head at a location spaced from said axis, said drive rod extending substantially parallel to said axis, said cutting head having a cutout on a proximal side in part for enabling a drawing of material in a proximal direction internally from a patient into a distal end of a tubular member upon a partial ejection of said cutting head from said distal end of said tubular member during a material removal operation, said material being severed in a scissor-type action of said cutting head against said distal end of said tubular member upon a drawing of said cutting head via said drive rod into said distal end of said tubular member, said cutting head having a maximal transverse cross-section conforming in a close fit to an inner surface of said tubular member, said cutting head being tapered from said maximal transverse cross-section in a proximal direction to facilitate a drawing of said cutting head into said distal end of said tubular member, said cutting head having an at least approximately semicylindrical outer surface located between said maximal transverse cross-section and a most proximal end of said cutting head for ensuring a locating of said drive rod eccentrically relative to said tubular member upon the drawing of said cutting head into the distal end of said tubular member.

2. The cutting member defined in claim 1 wherein said drive rod has a longitudinally extending lumen, an irrigation outlet being provided in one of said cutting head and said drive rod at a distal end thereof.

3. The cutting member defined in claim 2, further comprising an annular balloon attached to said cutting head on a distal side thereof, also comprising means for inflating said balloon.

4. The cutting member defined in claim 3 wherein said means for inflating includes a valve member attached to said cutting head for regulating fluid flow from said lumen into said balloon.

5. The cutting member defined in claim 4 wherein said valve member is spring loaded.

6. The cutting member defined in claim 5, wherein a wire extends to said valve member through said lumen.

7. The cutting member defined in claim 2 wherein said cutting head is hollow and said irrigation outlet is located in said cutting head.

8. The cutting member defined in claim 2 wherein said cutting head is solid.

9. The cutting member defined in claim 1 wherein said cutting head is provided with a rounded distal end.

10. The cutting member defined in claim 1 wherein said cutting head is partially cylindrical.

11. The cutting member defined in claim 1 wherein said cutting head is provided with a channel for the passage of a guide wire.

12. A medical method for removing material internal to a patient, comprising:

inserting a distal end portion of an introducer sheath into a patient, while maintaining a proximal end portion of said sheath outside the patient;

inserting a cutting head with a drive rod eccentrically attached to a proximal side thereof into said sheath, said drive rod being automatically disposed eccentrically inside said sheath in part by virtue of the eccentric attachment of said drive rod to said cutting head;

after insertion of the distal end portion of said sheath into the patient, ejecting at least a distal end portion of said cutting head from said sheath through an aperture in a distal end face of said sheath, thereby opening said aperture;

applying suction to said sheath to pull material from the patient into said sheath through the opened aperture;

after the pulling of material into said sheath, drawing said drive rod in a proximal direction to retract said cutting head into said sheath through said aperture, thereby severing material in said sheath from material outside said sheath, said drive rod again being automatically disposed eccentrically inside said sheath in part by virtue of the eccentric attachment of said drive rod to said cutting head; and applying suction to said sheath to remove the severed material from said sheath.

13. The method defined in claim 12, further comprising:

inserting a distal end portion of an ancillary instrument into the patient through said sheath and said aperture after said cutting head has been at least partially ejected from said sheath through said aperture;

actuating said ancillary instrument from outside the patient to effectuate an operation on material inside the patient; and after effectuating said operation, pulling said ancillary instrument in a proximal direction through the sheath to remove said ancillary instrument from the patient.

14. The method defined in claim 12 wherein said ancillary instrument includes a collapsed balloon at a distal end, further comprising inflating the balloon inside the patient, the actuating of said ancillary instrument including pulling the inflated balloon in a proximal direction towards said sheath, thereby drawing material internal to the patient towards said aperture.

15. The method defined in claim 12, further comprising feeding irrigation fluid via said drive rod to said sheath distally of the severed material to cooperate with the applied suction to form a pressure gradient across the severed material, thereby facilitating removal of the severed material from said sheath.

16. The method defined in claim 12 wherein said cutting head has an at least approximately semicylindrical outer surface extending from said drive rod on one side of said cutting head to a cutout on an opposite side of said cutting head, said outer surface conforming substantially to an inner surface of said sheath to ensure a locating of said drive rod eccentrically relative to said sheath upon a drawing of said cutting head into said sheath, thereby maximizing a cross-sectional area of said sheath during suction operation.

17. The method defined in claim 12 wherein an annular balloon is attached to said cutting head on a distal side thereof, also comprising inflating said balloon and drawing the inflated balloon in a proximal direction inside the patient.

18. The method defined in claim 17 wherein the inflating of said balloon includes opening a valve member attached to said cutting head and feeding fluid from a lumen of said drive member into said balloon.

19. A medical method for removing material internal to a patient, comprising:

inserting a distal end portion of a tubular member into a patient, while maintaining a proximal end portion of said tubular member outside the patient;

ejecting at least a distal end portion of a cutting head from said tubular member through an aperture in a distal end face of said tubular member, thereby opening said aperture;

after insertion of the distal end portion of said tubular member into the patient and after ejecting of the distal end portion of said cutting head from said tubular member, applying suction to said tubular member to pull material from the patient into said tubular member through the opened aperture;

after the pulling of material into said tubular member, drawing said cutting head in a proximal direction to pull said cutting head into and at least partways along said tubular member;

severing material in said tubular member from material outside said tubular member by virtue of the pulling of said cutting head through said aperture; and after the severing of said material, feeding irrigation fluid to said tubular member essentially upstream of the severed material to generate a pressure differential across the severed material to remove the severed material from said tubular member.

20. The method defined in claim 19 wherein the feeding of irrigation fluid to said tubular member includes the generating of positive pressure upstream of the severed material to forcibly eject the severed material from said tubular member.

21. The method defined in claim 19, further comprising:

inserting a distal end portion of an ancillary instrument into the patient through said tubular member and said aperture after said cutting head has been at least partially ejected from said tubular member through said aperture;

actuating said ancillary instrument from outside the patient to effectuate an operation on material inside the patient; and after effectuating said operation, pulling said ancillary instrument in a proximal direction through the tubular member to remove said ancillary instrument from the patient.

22. The method defined in claim 21 wherein said ancillary instrument includes a collapsed balloon at a distal end, further comprising inflating the balloon inside the patient, the actuating of said ancillary instrument including pulling the inflated balloon in a proximal direction towards said tubular member, thereby drawing material internal to the patient towards said aperture.

23. The method defined in claim 19 wherein said cutting head has an at least approximately semicylindrical outer surface extending from a drive rod on one side of said cutting head to a cutout on an opposite side of said cutting head, said outer surface conforming substantially to an inner surface of said tubular member to ensure a locating of said drive rod eccentrically relative to said tubular member upon a drawing of said cutting head into said tubular member, thereby maximizing a cross-sectional area of said tubular member during suction operation.

* * * * *